United States Patent
Sambursky

(10) Patent No.: US 12,078,636 B2
(45) Date of Patent: Sep. 3, 2024

(54) SELECTIVE WHITE BLOOD CELL LYSIS FOR IMMUNOASSAY SYSTEMS

(71) Applicant: Rapid Pathogen Screening, Inc., Sarasota, FL (US)

(72) Inventor: Robert P Sambursky, Lakewood Ranch, FL (US)

(73) Assignee: RAPID PATHOGEN SCREENING, INC., Sarasota, FL (US)

(*) Notice: Subject to any disclaimer, the term of this patent is extended or adjusted under 35 U.S.C. 154(b) by 0 days.

(21) Appl. No.: 17/786,245

(22) PCT Filed: Dec. 18, 2020

(86) PCT No.: PCT/US2020/065911
§ 371 (c)(1),
(2) Date: Jun. 16, 2022

(87) PCT Pub. No.: WO2021/127374
PCT Pub. Date: Jun. 24, 2021

(65) Prior Publication Data
US 2023/0026491 A1    Jan. 26, 2023

Related U.S. Application Data

(60) Provisional application No. 62/949,958, filed on Dec. 18, 2019.

(51) Int. Cl.
*G01N 33/543* (2006.01)
(52) U.S. Cl.
CPC .............. *G01N 33/54388* (2021.08)
(58) Field of Classification Search
CPC .......... G01N 33/558; G01N 33/54387; G01N 33/54388; G01N 33/54389; G01N 33/556;
(Continued)

(56) References Cited

U.S. PATENT DOCUMENTS 6,121,008 A * 9/2000 Fitzpatrick ....... G01N 33/54388
                                                      436/514
7,238,519 B2 * 7/2007 Bellet .............. G01N 33/54386
                                                      436/514
(Continued)

FOREIGN PATENT DOCUMENTS

WO     2014196803 A1    12/2014

OTHER PUBLICATIONS

"The Role of ethylenediamine tetraacetic acid (EDTA) as in vitro anticoagulant for diagnostic purposes", Clin. Chem Lab Med, 2007; 45(5); 565-576 (Year: 2007).*
(Continued)

*Primary Examiner* — Christopher L Chin
(74) *Attorney, Agent, or Firm* — Brown & Michaels, PC

(57) ABSTRACT

A test strip with selective white blood cell (WBC) lysis for release of WBC contents and the capture and holding of red blood cells (RBC), allowing for fast clearance and result interpretation and more accurate results at early time points due to the lack of red color interference caused by background red heme color of lysing of RBCs. The removal of the red color interference enhances both visual and digital interpretation of test strips, such as test strips of an immunoassay test. The test strip enhances the detection of both intracellular proteins of WBCs and extracellular proteins of RBCs simultaneously such as MxA and CRP, MxA and PCT, MxA and HNL, and MxA and IL-6, MxA and myeloid cells (STREM-1), MxA and angiopoietin 2, MxA and vascular endothelial growth factor (VEGF) or its soluble vascular endothelial growth factor receptor-1 (sVEGFR1), MxA and heparin binding protein (HBP) or other combinations.

21 Claims, 4 Drawing Sheets

(58) Field of Classification Search
CPC .................. G01N 33/72; G01N 33/721; B01L 2300/0825; Y10T 436/25125
USPC ....... 422/400, 401, 420, 421, 425, 426, 430; 435/287.7, 287.9, 970, 805, 810; 436/169, 170, 514, 518, 530, 810, 522, 436/66, 175
See application file for complete search history.

(56) References Cited

U.S. PATENT DOCUMENTS

| | | | | |
|---|---|---|---|---|
| 8,614,101 | B2* | 12/2013 | VanDine | B01L 3/5023 436/514 |
| 9,797,898 | B2* | 10/2017 | Babu | G01N 33/54388 |
| 9,857,365 | B2 | 1/2018 | Choi et al. | |
| 2002/0164670 | A1* | 11/2002 | Forrest | G01N 33/54388 435/7.93 |
| 2002/0192835 | A1* | 12/2002 | Cho | G01N 21/78 422/400 |
| 2010/0015634 | A1 | 1/2010 | Vandine et al. | |
| 2010/0297611 | A1* | 11/2010 | Sambursky | G01N 33/56983 435/5 |
| 2011/0104709 | A1 | 5/2011 | Yoshimizu et al. | |
| 2012/0220049 | A1 | 8/2012 | Bunce et al. | |
| 2012/0258469 | A1* | 10/2012 | Babu | G01N 33/56911 436/514 |
| 2012/0282634 | A1 | 11/2012 | Hughes et al. | |
| 2013/0022969 | A1 | 1/2013 | Kim et al. | |
| 2013/0196310 | A1* | 8/2013 | Sambursky | G01N 33/54388 435/7.1 |
| 2015/0099666 | A1* | 4/2015 | Sambursky | B82Y 30/00 435/7.1 |
| 2016/0245806 | A1* | 8/2016 | Sambursky | G01N 33/54388 |
| 2016/0266119 | A1 | 9/2016 | Sambursky et al. | |
| 2016/0349251 | A1 | 12/2016 | Hao et al. | |

OTHER PUBLICATIONS

International Search Report for PCT/US2020/065911 dated Mar. 16, 2021.

* cited by examiner

SELECTIVE WHITE BLOOD CELL LYSIS FOR IMMUNOASSAY SYSTEMS

BACKGROUND OF THE INVENTION

Field of the Invention

The invention pertains to the field of immunoassay systems. More particularly, the invention pertains to immunoassay systems with selective or preferential white blood cell lysis.

Description of Related Art

Most whole blood immunoassay systems hold back all blood cells, inclusive of both red blood cells and white blood cells using various filters to allow just the serum or plasma to pass through for testing. While this process is effective, it does not work for a system that simultaneously detects intracellular white blood cell proteins and extracellular serum or plasma components. In conventional assays, all blood cells within a whole blood sample are lysed releasing both the intracellular white blood cell proteins and heme of red blood cells which increases the red background of test strips red, which can both slow and obscure test results both for a visual interpretation or reading the results with an electronic reader. Conventional readers have implemented various techniques to overcome the red background, primarily by physically withholding all blood cells, and only allowing serum or plasma to pass through for protein detection.

SUMMARY OF THE INVENTION

An immunoassay for simultaneous detection of intracellular white blood cell (WBC) proteins and serum proteins.

A test strip with selective white blood cell (WBC) lysis for release of WBC contents and the simultaneous capture and holding of red blood cells (RBC), allowing for reduced background effects, faster clearance and result interpretation and more accurate results at early time points due to the lack of red color interference caused by background red heme color of lysing of RBCs. The removal of the red color interference enhances both visual and digital interpretation of test strips, such as immunoassay test strips. The test strip enhances the detection of both intracellular proteins of WBCs and extracellular proteins of RBCs simultaneously such as MxA and CRP, MxA and PCT, MxA and HNL, MxA and IL-6, MxA and myeloid cells (sTREM-1), MxA and heparin binding protein (HBP), or other combinations of intracellular and extracellular proteins.

In an embodiment of the present invention, the test strip of an immunoassay test has an absorbent pad, a blood separation pad, a conjugate pad and a membrane pad, all of which are adhered to a backing card. The absorbent pad overlaps with a blood separation pad. The blood separation pad overlaps with the conjugate pad and the conjugate pad overlaps with the membrane pad. No gaps are present between adjacent pads of the test strip. Selective lysis of the white blood cells takes place on the absorbent pad and any lysis of red blood cells and the associated heme is absorbed by the blood separation pad, allowing for a reduction in the red color interference present on the test strip, reducing the amount of time necessary for a visual and digital read of the test strip. The immunoassay test strip can be a lateral flow chromatography test strip or other immunoassay.

DETAILED DESCRIPTION OF THE INVENTION

Figure 1:
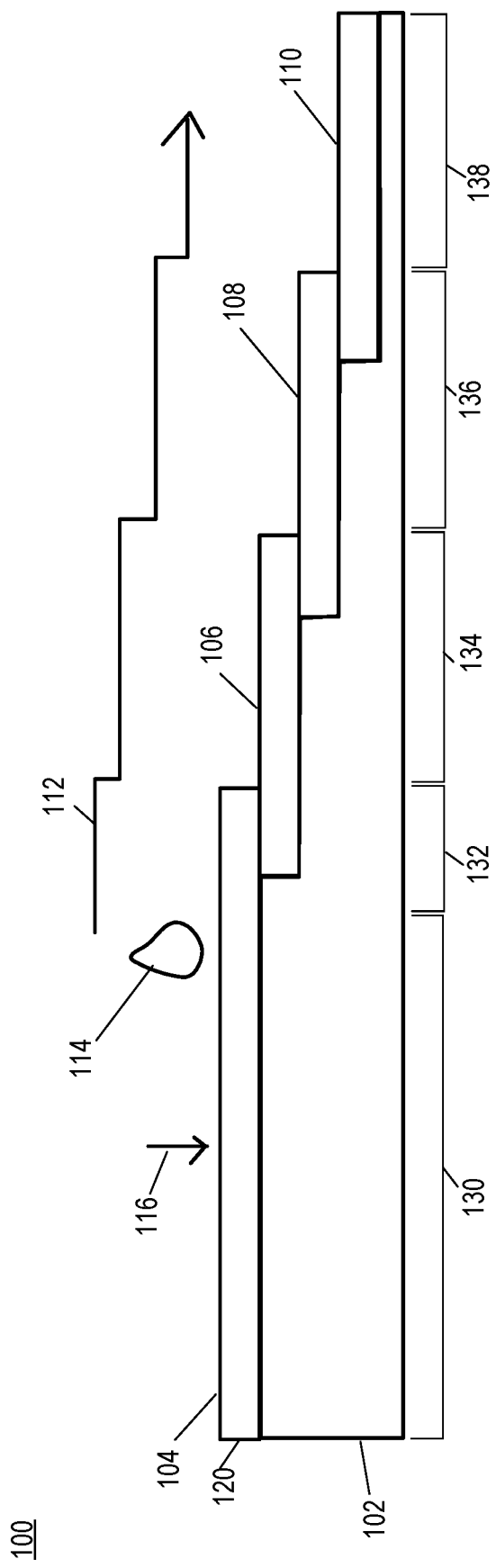
FIG. 1 shows a schematic of a test strip of an embodiment of the present invention with selective lysing of white blood cells.

FIG. 1 shows an example of an immunoassay test strip such as for a lateral flow immunoassay test which can be visually interpreted and digitally read by a reader. The immunoassay test strip may also be a test strip associated with: a radioimmunoassay (RIA), a counting Immunoassay (CIA), an enzyme Immunoassay (EIA), an enzyme-linked immunosorbent assay (ELISA), a fluoroimmnoassay (FIA), and a chemiluminescence immunoassay (CLIA).

The test may represent a single use disposable format and/or for use with a portable or desktop analyzer. The test strip 100 preferably includes an absorbent pad 104 of a length, a blood separation pad 106 of a length, a conjugate pad 108 of a length and a membrane pad 110 of a length, all of which are adhered to a hydrophobic backing card 102. Each of these pads has the capacity to transport fluid spontaneously. The absorbent pad 104 overlaps with the blood separation pad 106. The blood separation pad 106 overlaps with the conjugate pad 108 and the conjugate pad 108 overlaps with the membrane pad 110. Additionally, the test strip may contain a waste pad adjacent the membrane pad 110 to wick excess reagents and prevent backflow of any liquid. No gaps are present between adjacent pads of the test strip 100. A sample is provided on the absorbent pad 104 and flows to the membrane pad 110 in the direction shown by arrow 112 through capillary action.

The absorbent pad 104, the conjugate pad 108 and the membrane pad 110 are made of glass, natural fiber, polyester or a combination thereof. The blood separation pad 106 is preferably glass fibers or polyester fibers. The blood separation pad 106 may be the 6614 pad of Ahlstrom Munksjö USA Inc.

In one embodiment, the test strip 100 is at least 43 mm long, with the absorbent pad 104 being 15 mm in length, the blood separation pad 106 being 8 mm in length, the conjugate pad 108 being 8 mm in length and the membrane pad 110 being 12 mm in length. There is at least 2 mm of overlap between each of the pads. In one embodiment, the buffer solution delivery 116, the sample delivery of whole blood 114 and the selective white blood cell lysis occurs on the absorbent pad 104. The separation and capture of red blood cells occurs on the blood separation pad 106. The binding of the sample with biomarkers occurs on the conjugate pad 108. At least one test line and control line are present on the membrane pad 110.

In one embodiment, the buffer solution is delivered to the absorbent pad at approximately 7 mm from an end 120 of the absorbent pad 104. The sample of whole blood 114 is delivered to the absorbent pad 104 at approximately 11 mm from the end 120 of the absorbent pad 104. A lysis agent either present on the absorbent pad 104, in the buffer solution or in both the buffer solution and on the absorbent pad 104 and is located approximately 11 mm from the end 120 of the absorbent pad 104.

The test strip 100 preferably has a sample application zone 130, a lysis zone 132, a blood separation zone 134, a reagent zone 136 and a detection zone 138. The sample application zone 130 receives the whole blood sample 114 to be tested along with the running buffer solution 116 which causes the whole blood sample to flow through the test strip 100 in the direction of flow 112 shown by the arrow of FIG. 1.

The lysis zone 132 is preferably present on the absorbent pad 104. Lysis agents may be part of the test strip 100 or may be added to the running buffer, or a combination of using a test strip 100 with the lysis agent and the running buffer containing a lysis agent.

In one embodiment, the lysis agent is localized in the lysis zone 132 between the sample application zone 130 and the blood separation zone 134. The lysis agent is preferably soluble or miscible in the sample transport liquid, and the lysis agent is solubilized and activated upon contact with the sample transport liquid. The sample transport liquid then contains both lysis agent in solution or suspension and sample components in suspension. Any lysis-susceptible components in a sample, then being exposed in suspension to the lysis agent, are themselves lysed in situ. The running buffer then carries the sample, including any lysis-freed components, to the blood separation zone 134.

In other embodiments, the lysis zone 132 overlaps the sample application zone 130. In other embodiments, the lysis zone 132 overlaps the blood separation zone 134.

As to specific lysis agents, they may be grouped and selected based on their properties: salts, amphoteric and cationic agents, ionic and non-ionic detergents. The salt, Ammonium Chloride ($NH_4Cl$), lyses erythrocytes. Other salts, including, but not limited to, high concentrations of Sodium Chloride (NaCl) and Potassium Chloride (KCl), may rupture certain cell walls and membranes. Other lysis agents are amphoteric agents including, but not limited to, Lyso PC, CHAPS, and ZwittergentR. Alternatively, cationic agents including, but not limited to, C16 TAB and Benzalkonium Chloride may be used as a lysis agent. Both ionic and non-ionic detergents are often used to break or lyse the cell wall or cell membrane components such as lipoproteins and glycoproteins. Common ionic detergents include, but are not limited to, sodium dodecyl sulfate (SDS), Cholate, Sodium lauroyl sarcosinate (also known as sarkosyl) and Deoxycholate. Ionic detergents are good solubilizing agents. Antibodies retain their activity in 0.1% SDS or less. Common non-ionic detergents include, but are not limited to, Octylglucoside, Digitonin, saponin, C12E8, Lubrol™, Triton™ X-100, Noniodet P-40, NP-40 (for example TergitolR NP-40), Tween 20™, and Tween 80™. Non-ionic and mild ionic detergents are weaker denaturants and often are used to solubilize membrane proteins such as viral surface proteins. Additional lysis agents include, but are not limited to, urea and enzymes. Combinations of different lysis agents may be used to optimize the lysing environment.

In some preferred embodiments, Brij™ 35 or another polyoxyethylene may be used as the lysis agent on a lateral flow chromatography test strip. In other preferred embodiments, lysis agents are in a Tris-containing running buffer and include Brij™ 35 or another polyoxyethylene. In other preferred embodiments, lysis agents on the strip (including Brij™ 35 or another polyoxyethylene) and lysis agents in a Tris-containing running buffer (including Brij™ 35 or another polyoxyethylene) are used in combination. In yet other embodiments, an electromagnetic field can be applied to the sample to aid in selective lysis of the white blood cells. The application of the electromagnetic field can be used in conjunction with lysis agents on the test strip and/or lysis agents in the running buffer.

The running buffer additionally includes surfactants. Surfactants are generally wetting agents and lower the surface tension of a liquid. This then allows easier spreading by lowering the interfacial tension between liquids. Surfactants can interfere with the natural binding of antigen and antibody or ligand and receptors. The concentrations are, therefore, experimentally chosen for each class of lysis agent. Once lysis occurs, it is important that the desired binding reactions not be hindered. Generally, 0.001% lysis agent concentration is considered the lower limit, and the upper limit is approximately 1%. There is an additive or synergistic effect when combinations of lysis agents are used. This expands the working range of concentration to run from approximately 0.001% to 1%. In all cases, the total amount of lysis agent pre-loaded onto all locations of an individual test strip must be sufficient to lyse barriers of white blood cells to immunodetection, permitting practical operation of the test strip.

The lysis agent itself should not interfere with any other assay detector or indicator agents and thus does not interfere with any other assay interactions and reactions to such an extent as to prevent practical operation of the assay. The lysis agent should have sufficient shelf life to allow manufacture, distribution and storage before use of a test strip in point-of-care testing. In embodiments of the present invention, the lysis is specifically targeting white blood cells.

The surfactant solutions are preferably in a range of 0.1%-1.0% of the running buffer and can include one or more of octylphenoxy polyethoxyethanol (Triton™ X-100), n-nonyl phenoxy polyglycerol (Olin Chemicals 10GR), polyethylene glycol ester of a secondary alcohol (Tergitol® 15-D-12), polyoxyethylene lauryl ether (Brij™ 35), polyoxyethylene stearate, saponin, and digitonin. The addition of the surfactant solutions to the buffer additionally enhance the speed of blood clearance of heme from any lysed red blood cells on the test strip 100. In a preferred embodiment, the buffer solution used is Tris with Brij™-35 or another polyoxyethylene.

Since some lysis of the RBCs of the whole blood sample may occur, red blood cell membrane stabilizers may be added to the running buffer and/or be present at the lysis zone 132. The RBC membrane stabilizers can include, but is not limited to mannitol, citrate, Ethylenediaminetetraacetic acid (EDTA), or Horseradish peroxidase (HRP) conjugate stabilizer (StabilZyme®) alone or in combination with a sugar or protein attachment or antibodies. Further stabilization of the red blood cell membrane with stabilizers can enhance signal by reducing the background, causing by lysing of the RBCs. In some embodiments, RBC stabilizing agents could additionally be present in the blood separation pad.

The blood separation zone 134 is preferably present on the blood separation pad 106. The blood separation pad 106 absorbs heme from any of the RBCs which did lyse, and in some embodiments due to the size of the intact RBCs, capture the RBCs. The physical capture of the RBCs in the blood separation zone 134 can be accomplished through reduced membrane porosity and/or glass beads incorporated into the blood separation pad 106. In other embodiments, physical capture of the RBCs in the blood separation zone may be accomplished through specific binding of a ligand, including, but not limited to an antibody or lectin. The absorption of heme and the capture of the intact red blood cells removes any red background color that may be present on the test strip to allow for easy visual reading of test results and reading of results by a reader. Furthermore, by reducing the red color associated with the background of the test strip from the heme, the results of the test strip can be visually and digitally read in less than 10 minutes. In some embodiments, the test strip results can be visually and digitally read in less than 8 minutes or less. The blood separation pad 106 preferably reduces the heme from any lysed RBCs present by at least 10-20%.

The reagent zone 136 is aligned with the conjugate pad 108 and contains at least one labeled binding partner that binds to a combination of intracellular and extracellular biomarkers or proteins such that bound proteins marks target particles as they pass through the conjugate pad 108 as they continue across to the membrane pad 110 containing test and control lines in the detection zone 138. The intracellular and extracellular proteins simultaneously detected can include, but is not limited to myxovirus resistance protein A (MxA) and C-Reactive Protein (CRP), MxA and procalcitonin (PCT), MxA and human neutrophile lipocalin (HNL), and MxA and Interleukin-6 (IL-6), MxA and myloid cells (STREM-1), MxA and angiopoietin 2, MxA and vascular endothelial growth factor (VEGF) or its soluble vascular endothelial growth factor receptor-1 (sVEGFR1), and MxA and heparin binding protein (HBP) or other combination of intracellular and extracellular proteins. The intracellular and extracellular biomarkers may indicate a viral marker and at least one labeled binding partner that binds to and indicates a bacterial marker that are eluted by and then able to migrate with a sample transport liquid (e.g. a buffer solution). The labeled binding partners are capable of specifically binding to a viral or bacterial marker of interest to form a complex which in turn is capable of specifically binding to another specific reagent or binding partner in the detection zone 138.

In one embodiment, a running buffer including 0.01% to 1.0% of surfactant solutions selected from octylphenoxy polyethoxyethanol (Triton™ X-100), n-nonyl phenoxy polyglycerol (Olin Chemicals 10G), polyethylene glycol esther of a secondary alcohol (Tergitol® 15-D-12), polyoxyethylene lauryl ether (Brij™ 35) and polyoxyethylene stearate, saponin and digitonin is added to the absorbent pad along with the whole blood sample in the sample application zone 130. The running buffer solution is preferably Tris with Brij™-35 or another polyoxyethylene. The WBC of the whole blood sample are lysed in the lysis zone 132 on the absorbent pad 104. The proteins from the lysing of the WBCs and the RBCs of the whole blood sample flow to the blood separation pad 106 of the blood separation zone 134. The heme associated with lysed RBCs is preferably separated from the sample and absorbed by the blood separation pad 106. Whole RBCs may be physically captured within the blood separation zone 134. The intracellular proteins of the lysed WBCs and the extracellular proteins associated with the RBCs flow from the blood separation pad 106 to the conjugate pad 108 of the reagent zone 136, wherein the intracellular proteins of the WBCs and extracellular proteins of the RBCs can bind to biomarkers. The proteins which are bound to biomarkers and unbound proteins flow through the conjugate pad to the membrane pad and over at least one test line and control line.

Example

Three samples were each run on a test strip containing an absorbent pad, a blood separation pad of a 6614 absorbent pad, a conjugate pad and a membrane.

| Sample | Contents |
| --- | --- |
| 1 | Tris buffer (TB) |
| 2 | Uninduced human interferon-α (−I) |
| 3 | Induced human interferon-α (+I) containing MxA |

The first sample was buffer only, the second sample was an uninduced human interferon-α (−I) or negative sample and a third sample of an induced (+I) human interferon-α, positive MxA blood sample.

Each 95 μL of samples 1-3 received 5 μL of thirty percent stock of Brij™ L23 (1.5% concentration). A 10 μL sample of samples 1-3 were each delivered to the absorbent pad of the three test strips. 85 μL of Tris buffer with pH 9.0 was then added to the absorbent pad of the three test strips. Each of the test strips was then read at 10 minutes.

Figure 2:
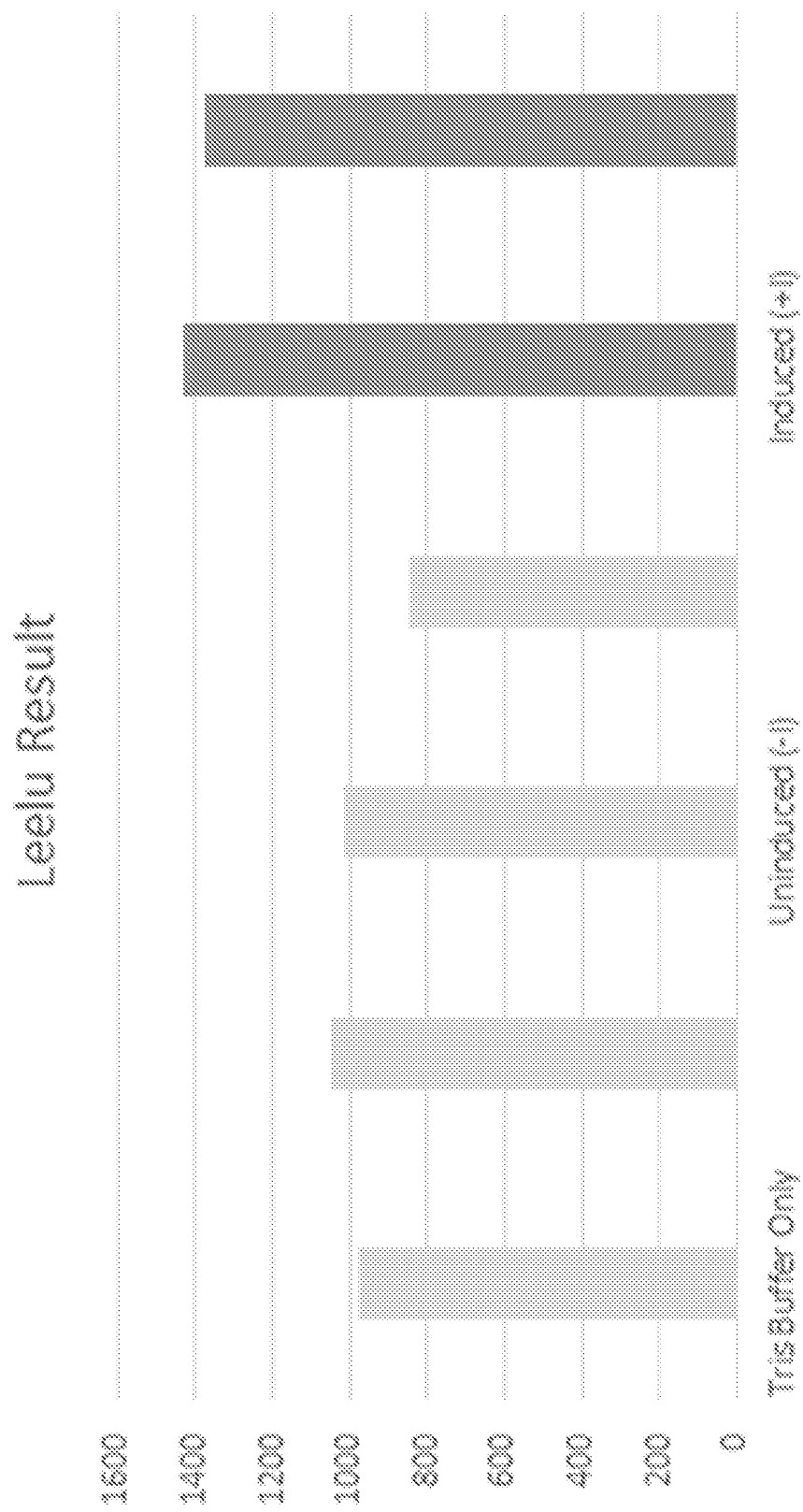
FIG. 2 shows a graph of test line color intensity for tris buffer applied to two test strips, an uninduced blood sample applied to two test strips and an induced blood sample applied to two test strips.
Figure 3:
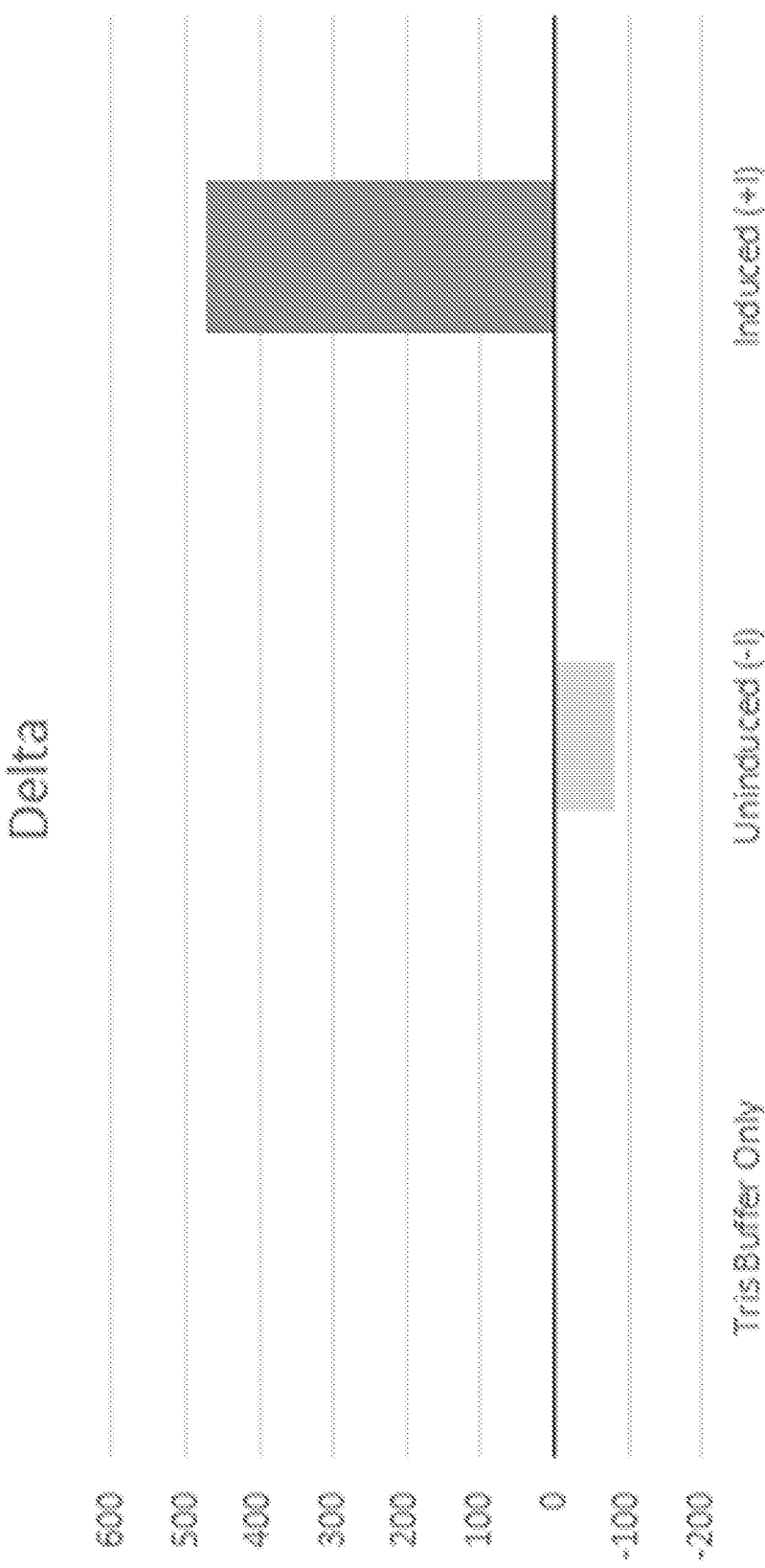
FIG. 3 shows a graph of the change in test line color intensity of uninduced and induced blood samples relative to the tris buffer samples.
Figure 4:
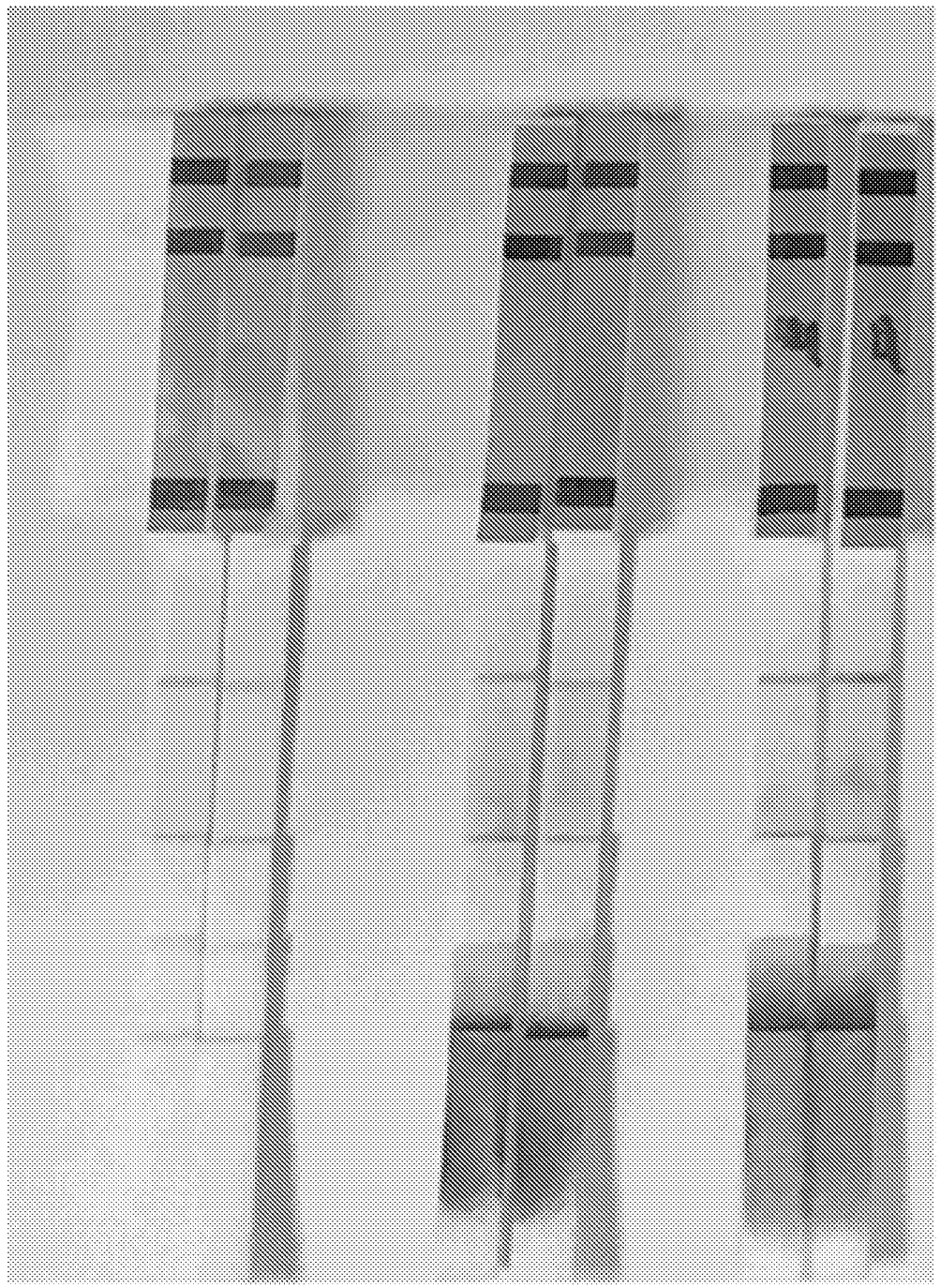
FIG. 4 shows the six test strips with tris buffer applied to two test strips, an uninduced blood sample applied to two test strips and an induced blood sample applied to two test strips.

The results are summarized in FIGS. 2 and 3. FIG. 2 shows the MxA signal for each sample as measured by a camera-based test strip reader of tris buffer applied to two test strips, an uninduced blood sample applied to two test strips and an induced blood sample applied to two test strips. FIG. 3 shows a graph of the change in test line color intensity of uninduced and induced blood samples relative to the tris buffer samples. The six test strips are shown in FIG. 4, two for each sample.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. An immunoassay test strip with a first end and a second end, wherein fluid flows through capillary action downstream from the first end to the second end, the immunoassay test strip comprising:
   an absorbent pad for receiving a blood sample for testing and selectively lysing at least white blood cells of the blood sample;
   a blood separation pad downstream of the absorbent pad for withholding intact red blood cells or removing red heme from any lysed red blood cells of the blood sample, comprising at least one filter with a nitrocellulose pore size to withhold the intact red blood cells or the red heme, reducing red color interference caused by red heme background color on the immunoassay test strip by at least 10-20%;
   a conjugate pad downstream of the blood separation pad containing biomarkers for binding to intracellular proteins of the white blood cells and extracellular proteins of the red blood cells within the blood sample; and
   a membrane pad having at least one test line and control line for indicating results of the presence of intracellular proteins of the white blood cells and extracellular proteins of the red blood cells within the blood sample;
   wherein the sample flows downstream from the first end to the second end from the absorbent pad, to the blood separation pad, to the conjugate pad and to the membrane pad;
   wherein the results are discernable in ten minutes or less.

2. The immunoassay test strip of claim 1, wherein the results indicate that biomarkers corresponding to a pair including the intracellular proteins of the white blood cells and the extracellular proteins of the red blood cells is selected from a group of pairs consisting of: a pair of myxovirus resistance protein A (MxA) and C-Reactive Protein (CRP), a pair of MxA and procalcitonin (PCT), a pair of MxA and human neutrophile lipocalin (HNL), a pair of MxA and Interleukin-6 (IL-6), a pair of MxA and myloid cells (sTREM-1), a pair of MxA and angiopoietin 2, a pair of MxA and vascular endothelial growth factor (VEGF), a pair of MxA and soluble vascular endothelial growth factor receptor-1 (sVEGFR1), and a pair of MxA and heparin binding protein (HBP).

3. An immunoassay test strip with a first end and a second end, wherein fluid flows through capillary action downstream from the first end to the second end, the immunoassay test strip comprising:
   an absorbent pad for receiving a blood sample for testing and selectively lysing at least white blood cells of the blood sample;
   a blood separation pad downstream of the absorbent pad for withholding intact red blood cells or removing red heme from any lysed red blood cells of the blood sample, comprising glass beads to bind to intact red blood cells or remove red heme from any lysed red blood cells of the blood sample, reducing red color interference caused by red heme background color on the immunoassay test strip by at least 10-20%;
   a conjugate pad downstream of the blood separation pad containing biomarkers for binding to intracellular proteins of the white blood cells and extracellular proteins of the red blood cells within the blood sample; and
   a membrane pad for indicating results of the presence of intracellular proteins of the white blood cells and extracellular proteins of the red blood cells within the blood sample;
   wherein the sample flows downstream from the first end to the second end from the absorbent pad, to the blood separation pad, to the conjugate pad and to the membrane pad;
   wherein the results are discernable in ten minutes or less.

4. The immunoassay test strip of claim 3, wherein results of the sample are visually read.

5. The immunoassay test strip of claim 3, wherein the results of the sample are digitally read.

6. The immunoassay test strip of claim 3, wherein the absorbent pad further comprises a lysis agent.

7. The immunoassay test strip of claim 3, further comprising running buffer which contains red blood cell membrane stabilizers.

8. The immunoassay test strip of claim 7, wherein the red blood cell membrane stabilizers are selected from a group consisting of: mannitol, citrate, Ethylenediaminetetraacetic acid, and Horseradish peroxidase conjugate stabilizer, Horseradish peroxidase conjugate stabilizer with a sugar, Horseradish peroxidase conjugate stabilizer with a protein attachment and Horseradish peroxidase conjugate stabilizer with antibodies.

9. The immunoassay test strip of claim 8, wherein the running buffer contains 0.1%-1.0% of surfactants selected from a group consisting of: octylphenoxy polyethoxyethanol (Triton™ X-100), n-nonyl phenoxy polyglycerol (Olin Chemicals 10GR), polyethylene glycol ester of a secondary alcohol (Tergitol™ 15-D-12), polyoxyethylene lauryl ether (Brij™ 35), polyoxyethylene stearate, saponin and digitonin.

10. An immunoassay test strip with a first end and a second end, wherein fluid flows through capillary action downstream from the first end to the second end, the immunoassay test strip comprising:
    an absorbent pad for receiving a blood sample, the absorbent pad comprising a length, wherein along the length is a first location with buffer solution and a second location for whole blood and lysis agent;
    a blood separation pad downstream of the absorbent pad, comprising at least one filter with a nitrocellulose pore size such that intact red blood cells are withheld or remove red heme from any lysed red blood cells of the blood sample, reducing red color interference caused by red heme background color on the immunoassay test strip by at least 10-20%;
    a conjugate pad downstream of the blood separation pad containing at least one labeled binding partner that binds to a combination of intracellular proteins and extracellular proteins of the red blood cells within the blood sample; and
    a membrane pad having at least one test line and control line indicating results of a presence of the intracellular proteins of the white blood cells and the extracellular proteins of the red blood cells within the blood sample;
    wherein the sample flows downstream from the first end to the second end from the absorbent pad, to the blood separation pad, to the conjugate pad and to the membrane pad;
    wherein the results are discernable in ten minutes or less.

11. The immunoassay test strip of claim 10, wherein the blood separation pad captures whole, unlysed red blood cells within the at least one filter with the nitrocellulose pore size configured to withhold intact red blood cells within the blood separation pad.

12. The immunoassay test strip of claim 10, wherein the blood separation pad reduces the heme by at least 20% by capturing heme the at least one filter with nitrocellulose pore size for withholding heme within the blood separation pad.

13. The immunoassay test strip of claim 10, wherein results of the sample are visually read.

14. The immunoassay test strip of claim 10, wherein the results of the sample are digitally read.

15. The immunoassay test strip of claim 14, wherein the absorbent pad further comprises a lysis agent.

16. The immunoassay test strip of claim 14, further comprising running buffer which contains red blood cell membrane stabilizers.

17. The immunoassay test strip of claim 16, wherein the red blood cell membrane stabilizers are selected from a group consisting of: mannitol, citrate, Ethylenediaminetetraacetic acid, and Horseradish peroxidase conjugate stabilizer, Horseradish peroxidase conjugate stabilizer with a sugar, Horseradish peroxidase conjugate stabilizer with a protein attachment and Horseradish peroxidase conjugate stabilizer with antibodies.

18. The immunoassay test strip of claim 16, wherein the running buffer contains 0.1%-1.0% of surfactants selected from a group consisting of: octylphenoxy polyethoxyethanol (Triton™ X-100), n-nonyl phenoxy polyglycerol (Olin Chemicals 10GR), polyethylene glycol ester of a secondary alcohol (Tergitol™ 15-D-12), polyoxyethylene lauryl ether (Brij™ 35), polyoxyethylene stearate, saponin and digitonin.

19. The immunoassay test strip of claim 10, wherein the results indicate that biomarkers corresponding to a pair including the intracellular protein of the white blood cells and the extracellular protein of the red blood cells is selected from a group of pairs consisting of: a pair of myxovirus resistance protein A (MxA) and C-Reactive Protein (CRP), a pair of MxA and procalcitonin (PCT), a pair of MxA and human neutrophile lipocalin (HNL), a pair of MxA and Interleukin-6 (IL-6), a pair of MxA and myloid cells (sTREM-1), a pair of MxA and angiopoietin 2, a pair of MxA and vascular endothelial growth factor (VEGF), a pair of MxA and soluble vascular endothelial growth factor receptor-1 (sVEGFR1), and a pair of MxA and heparin binding protein (HBP).

20. The immunoassay test strip of claim 10, wherein the test strip is associated with an immunoassay selected from a group consisting of: a radioimmunoassay (RIA), a counting Immunoassay (CIA), an enzyme Immunoassays (EIA), an enzyme-linked immunosorbent assays (ELISA), a fluoro-immnoassay (FIA), and a chemiluminescence immunoassay (CLIA).

21. The immunoassay test strip of claim 10, wherein the test strip is a lateral flow chromatography test strip.

\* \* \* \* \*